United States Patent
Steen

(10) Patent No.: US 7,226,427 B2
(45) Date of Patent: Jun. 5, 2007

(54) SYSTEMS AND PROCEDURES FOR TREATING CARDIAC ARREST

(75) Inventor: Stig Steen, Lund (SE)

(73) Assignee: Jolife AB, Lund (SE)

(*) Notice: Subject to any disclaimer, the term of this patent is extended or adjusted under 35 U.S.C. 154(b) by 502 days.

(21) Appl. No.: 10/456,088

(22) Filed: Jun. 6, 2003

(65) Prior Publication Data
US 2004/0230140 A1 Nov. 18, 2004

Related U.S. Application Data

(60) Provisional application No. 60/470,229, filed on May 12, 2003.

(51) Int. Cl.
*A61H 31/00* (2006.01)
*A61M 16/00* (2006.01)
(52) U.S. Cl. ............. 601/44; 601/DIG. 10; 128/204.18
(58) Field of Classification Search .................. 601/41, 601/44; 128/204.18
See application file for complete search history.

(56) References Cited

U.S. PATENT DOCUMENTS

| | | | |
|---|---|---|---|
| 1,193,476 A | 8/1916 | Block | |
| 2,067,268 A | 1/1937 | Hans | |
| 2,071,215 A | 2/1937 | Peterson | 601/41 |
| 3,364,924 A | 1/1968 | Barkalow | |
| 3,374,783 A | 3/1968 | Hurvitz | 601/97 |
| 3,425,409 A | 2/1969 | Isaacson et al. | 601/41 |
| 3,509,899 A * | 5/1970 | Hewson | 601/41 |
| 3,610,233 A * | 10/1971 | Barkalow | 601/41 |
| 3,644,943 A | 2/1972 | Parodi fu Leonardo et al. | 4/255 |
| 3,985,126 A | 10/1976 | Barkalow | |
| 4,059,099 A | 11/1977 | Davis | |
| 4,273,114 A | 6/1981 | Barkalow et al. | |
| 4,338,924 A | 7/1982 | Bloom | |
| 4,895,173 A | 1/1990 | Brault et al. | 128/870 |
| 4,928,674 A * | 5/1990 | Halperin et al. | 601/44 |
| 5,287,846 A | 2/1994 | Capjon et al. | |

(Continued)

FOREIGN PATENT DOCUMENTS

EP  0 509 773  10/1992

(Continued)

OTHER PUBLICATIONS

"Development of a Cardiopulmonary Resuscitation Vest Equipped With a Defibrillator," T. Tsuji et al., Engineering in Medicine and Biology Society, Proceedings of the 20th Annual International Conference of the IEEE Engineering in Medicine and Biology Society, vol. 20, No. 1, 1998, pp. 426-427.

(Continued)

*Primary Examiner*—Danton DeMille
(74) *Attorney, Agent, or Firm*—Fish & Neave IP Group, Ropes & Gray LLP; Jeffrey C. Aldridge

(57) ABSTRACT

Improved procedures for cardiopulmonary resuscitation of a victim of cardiac arrest are provided. In the resuscitation, the victim's chest is mechanically compressed and decompressed to stimulate the heart. The victim is induced to inspire and expire against insufflating breathing gas during the chest compression/decompressions. The breathing gases are adduced under pressure to promote the development of a positive coronary perfusion pressure.

Electro-stimulation of the heart can be carried after positive coronary perfusion pressures have been achieved. The electro-stimulation can be defibrillation or heart pacing or both. The chest compression/decompression cycles and the electro-stimulation measures are synchronized to promote sufficiently body circulation of oxygenated blood in a subject suffering from cardiac arrest. Medical equipment systems are provided for implementing the CPR procedures.

74 Claims, 7 Drawing Sheets

U.S. PATENT DOCUMENTS

| | | | |
|---|---|---|---|
| 5,454,779 A | 10/1995 | Lurie et al. | 601/43 |
| 5,492,115 A * | 2/1996 | Abramov et al. | 128/205.24 |
| 5,634,886 A | 6/1997 | Bennett | 601/41 |
| 5,645,522 A | 7/1997 | Lurie et al. | 601/43 |
| 5,738,637 A | 4/1998 | Kelly et al. | 601/41 |
| 6,171,267 B1 | 1/2001 | Baldwin et al. | 601/106 |
| 6,174,295 B1 | 1/2001 | Cantrell et al. | 601/41 |
| 6,213,960 B1 | 4/2001 | Sherman et al. | 601/41 |
| 6,312,399 B1 | 11/2001 | Lurie et al. | 601/41 |
| 6,533,739 B1 | 3/2003 | Palmer et al. | 601/41 |
| 2002/0026131 A1 | 2/2002 | Halperin | 601/41 |
| 2004/0039313 A1* | 2/2004 | Sherman et al. | 601/21 |
| 2005/0016541 A1* | 1/2005 | Lurie et al. | 128/205.24 |

FOREIGN PATENT DOCUMENTS

| | | |
|---|---|---|
| EP | 0 623 334 A1 | 11/1994 |
| EP | 0 623 334 B1 | 6/1999 |
| FR | 1476518 | 12/1964 |
| FR | 2382889 | 3/1977 |
| GB | 1187274 | 4/1970 |

OTHER PUBLICATIONS

"Active Compression-Decompression, A New Method of Cardiopulmonary Resuscitation", Todd J. Cohen et al., JAMA (The Journal of the American Medical Association), vol. 267, No. 21, Jun. 3, 1992.

"The Critical Importance of Minimal Delay Between Chest Compressions and Subsequent Defibrillation: a Haemodynamic Explanation", Stig Steen et al., Resuscitation, vol. 58(3), Sep. 2003.

"Time for Change?", Douglas Chamberlain and Michael Colquhoun, Resuscitation, vol. 58(3), Sep. 2003.

* cited by examiner

SYSTEMS AND PROCEDURES FOR TREATING CARDIAC ARREST

This application claims the benefit of U.S. provisional application No. 60/470,229 filed May 12, 2003.

BACKGROUND OF THE INVENTION

The present invention relates to apparatus and procedures for medically responding to an abnormal cardiac event in a subject. In particular, the present invention relates to the emergency medical care of a subject or victim of cardiac arrest.

Cardiac arrest is an event in which a subject's heart abruptly or suddenly stops. The accompanying symptoms and often-unnoticed precursors of cardiac arrest include various heart arrhythmias (e.g., ventricular tachycardia or fibrillation, asystolia, and Pulseless Electrical Activity (PEA)). Other causes of cardiac arrest may include atherosclerotic heart disease, profound anaphylactic shock, major changes in the blood's electrolyte composition, or drug overdose.

Unattended cardiac arrest is generally fatal within a few minutes. However, prompt medical attention can have positive outcomes. If circulation of oxygenated blood through the body is re-established within a few minutes of cardiac arrest, then irreversible ischemic (lack of oxygen) damage to body tissue may be minimized or avoided.

In the common or traditional cardiopulmonary resuscitation (CPR) treatments, the victim or subject's heart is externally massaged or stimulated in order to recirculate blood through the subject's body. The subject is ventilated to provide airflow through the lungs for blood oxygenation. Further, a defibrillator, which sends a strong electric current through the heart, may be used to eliminate the arrhythmic impulses.

Traditionally, medically trained persons or resuscitators are required to administer or deliver CPR. Traditional CPR is delivered manually by alternately compressing the subject's chest by hand in a cyclical fashion, and breathing mouth-to-mouth into the subject's airways. Guidelines published by the European Resuscitation Council and the American Heart Association recommend a chest compression of about 20% of the sternum depth. The adult sternum depth can vary from about 175 mm to 260 mm. Thus, chest compression depths of 35 to 52 mm are recommended. Manually administering chest compressions of these depths can be strenuous and physically demanding, making it difficult to give CPR consistently or properly. Now automated chest compression/decompression devices (CPR devices) are available to mechanically stimulate the heart. These devices compress and decompress a subject's chest in a cyclical fashion. These devices may be incorporated in field portable CPR assemblies or systems (such as the LUCAS™ devices that are sold by assignee Jolife AB of Lund, Sweden).

The automated chest compression/decompression or CPR devices include a pneumatically driven compressor unit, which reciprocally drives a chest contact pad to mechanically compress and/or decompress the subject's chest. The subject is rested in a supine position during CPR administration. The compressor unit is mechanically supported vertically above the subject's chest so that the contact pad is in mechanical contact with the subject's chest about the sternum.

Other useful medical devices (e.g., defibrillators, and pacers) also can be used with the automated CPR devices for additional therapeutic measures. For example, electrical defibrillators may be used to defibrillate the subject's heart separately or in combination with mechanical stimulation of the heart. Barkalow et al. U.S. Pat. No. 4,273,114 describes, for example, an apparatus that may be used for concurrent mechanical chest compression and defibrillation.

Respiratory arrest or otherwise diminished respiratory function often accompanies cardiac arrest. Restoring an adequate supply of oxygen through the subject's airways to oxygenate venous blood is as crucial for the subject's resuscitation as it is to recirculate blood through the subject's body by chest compression/decompressions. In traditional CPR administrations, the resuscitator breathes or blows into the subject's mouth to deliver oxygen into the lungs. Now, ventilation devices or aids are available for use during CPR administrations to improve or time the flow of oxygen to the lungs. Lurie et al. U.S. Pat. No. 6,312,399 B1 describes, for example, an electro stimulator for stimulation of the subject's respiratory muscles during the CPR chest compression/decompressions. The stimulation of respiratory muscles causes the subject to gasp. This gasping increases the magnitude and duration of negative intrathoracic pressure (chest decompression) by which venous blood is drawn to the heart and lungs. The respiratory muscle stimulation may be electronically timed to occur during the mechanical chest decompression phase to match the gasping inspiration of air with the draw of venous blood.

Similarly, Lurie et al. U.S. Pat. No. 5,692,498 discloses use of a pressure check valve to time air flow into a subject's lungs. The pressure check valve is supported in an endotracheal tube, which is installed in the subject's trachea. The valve allows air inflow only when the lung cavity or intrathoracic pressures fall below a threshold pressure, for example, during chest decompression. Accordingly, inflows of oxygenating air during CPR administration can be timed to occur at the same times as when venous blood flow is drawn into the heart by the low intrathoracic pressures.

Consideration is now being given generally to ways of improving or enhancing the efficacy of CPR measures or treatments. Attention is directed to non-invasive techniques and apparatus for oxygenating blood and re-establishing blood flow or circulation in a subject who is a victim of cardiac arrest.

SUMMARY OF THE INVENTION

In accordance with the principles of the invention, non-invasive CPR procedures are provided. The CPR procedures can be used for re-establishing body circulation of oxygenated blood in a subject suffering from cardiac arrest. Medical equipment systems are provided for implementing the CPR procedures.

In the inventive CPR procedures, a breathing gas under positive pressure is applied to the airways of the subject. The breathing gas supply to the subject's airways may, for example, be set up through an endotracheal delivery tube or through a gas mask, which covers the mouth and/or nose of the subject. The breathing gas may be oxygen or a suitable oxygen-inert gas mixture. Additionally, the breathing gas may carry suitable medications, which are beneficially administered to the subject. The medications may include, for example, cardioplegic solutions (such as disclosed in International Patent Publication WO 02/11741) for alleviating the effect of cardiac arrest, medications for encouraging recirculation (e.g., adrenaline, and non-adrenaline, vasodilators, vasopressin, cortisone, insulin, or cyclosporin A), and cooling salines. The medications may be introduced into the breathing gas in the form of an aqueous spray or as a mist.

The subject's heart is mechanically stimulated or externally massaged using a compressor/decompressor device. The compression/decompression cycle rates may be suitably configured or chosen as medically appropriate. Suitable cycle rates may, for example, be in the range of about 60 cycles per minute to 200 cycles per minute. During the mechanical stimulation, the subject is induced to inspire and expire against the positive pressure of the applied breathing gas to encourage development of a positive aortic-to-right atrial pressure gradient (coronary perfusion pressure, CPP).

After a positive CPP is established, the subject's heart optionally may be subject to electro stimulation using suitable electrodes placed, for example, on the subject's chest and back. Electro stimulation may, for example, be administered in the form of electrical pacing pulses or defibrillating shock, or a combination of both. The electro stimulation may be administered while continuing with the application of positive pressures of breathing gas, and while continuing with mechanical stimulation of the heart. However, in some cases, the CPR procedure after establishing a positive CPP may be suitably modified to alternate periods of electro stimulation with periods of mechanical stimulation.

The compressor unit used for mechanical stimulation may be pneumatically driven. The same breathing gas that is applied to the airways of the subject can be used first for driving the compressor unit. A convenient source of breathing gas, for example, a compressed gas tube or pressurized gas container, may be used to drive a reciprocating shaft of a pneumatic cylinder in the compressor unit. Gas, which is vented or exhausted from the pneumatic cylinder, can be reused for supply as breathing gas to the subject's airways.

In the CPR procedure, the timing and the strength of the compression/decompression cycles, the timing of electro stimulation, and other medical measures or activities are synchronized with each other to increase the efficacy of the procedure. In an exemplary CPR procedure, the pneumatic drive arrangement in the compressor unit is configured to administer abrupt compression and decompression cycles with quick or abrupt rise and fall times. The compression/decompression cycles and the corresponding intrathoracic pressures have shapes in time that are approximately trapezoidal. Relatively flat static compression and decompression phases are maintained between quick or abrupt transitions. The positive breathing gas pressure is adduced at least through the decompression phases to encourage development of a positive CPP.

Electro-simulation by heart pacing or defibrillating shock may be initiated once a threshold CPP of about 10 mg Hg or more is achieved. Defibrillation may be induced in the later portions of the static chest compression phases. If electro simulation by pacing is preferred, pacing currents may be applied during early portions of the chest compression phases.

BRIEF DESCRIPTION OF THE DRAWINGS

Further features of the invention, its nature, and various advantages will be more apparent from the following detailed description of the preferred embodiments and the accompanying drawings, wherein like reference characters represent like elements throughout, and in which:

FIG. 1b is a sectional view taken along direction A-A of FIG. 1a;

DETAILED DESCRIPTION OF THE INVENTION

The present disclosure provides solutions for improving CPR procedures that are used to treat victims or subjects of cardiac arrest. A disclosed solution integrates the administration of chest compression/decompression, ventilation and other therapeutic measures (e.g. electro stimulation). In an integrated CPR procedure, the administration of these and other measures to a subject is co-ordinated or synchronized to promote better recovery.

Other aspects of the present invention relate to integrating or linking various medical equipment and monitoring devices in a system for implementing or administering the integrated CPR procedures.

The medical equipment system used for administering the inventive CPR procedures may include automated compression/decompression devices or assemblies that are designed for use either in the hospital or in the field. Portable chest compression assemblies for field use by emergency response personnel are disclosed, for example, in co-pending and co-assigned U.S. patent application Ser. No. 10/105,054 filed Mar. 2, 2002, which is incorporated by reference in its entirety herein.

Figure 1A:
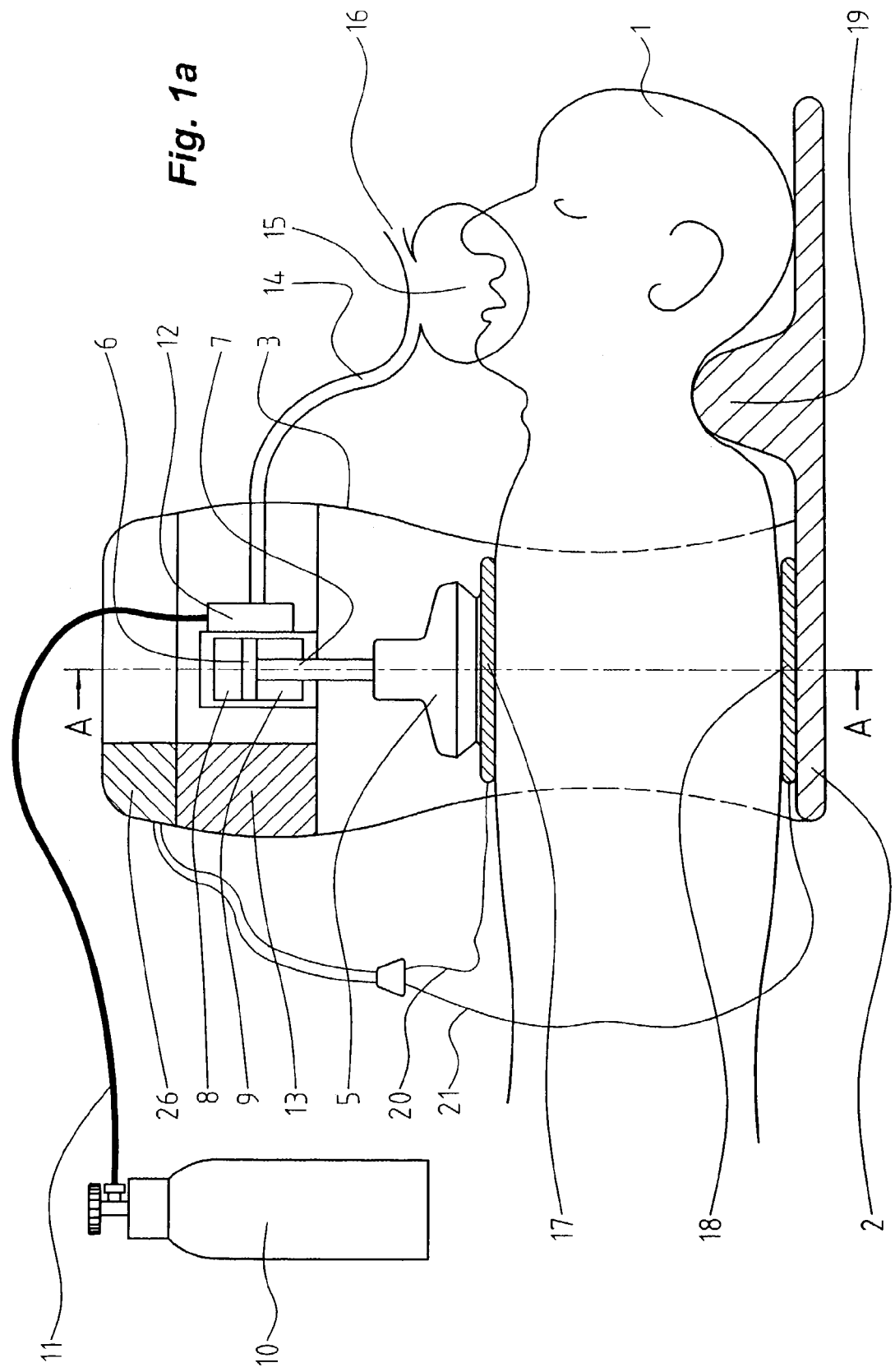
FIG. 1a is a schematic side view of a CPR system apparatus used to administer CPR to a subject, in accordance with the present invention.
Figure 1B:
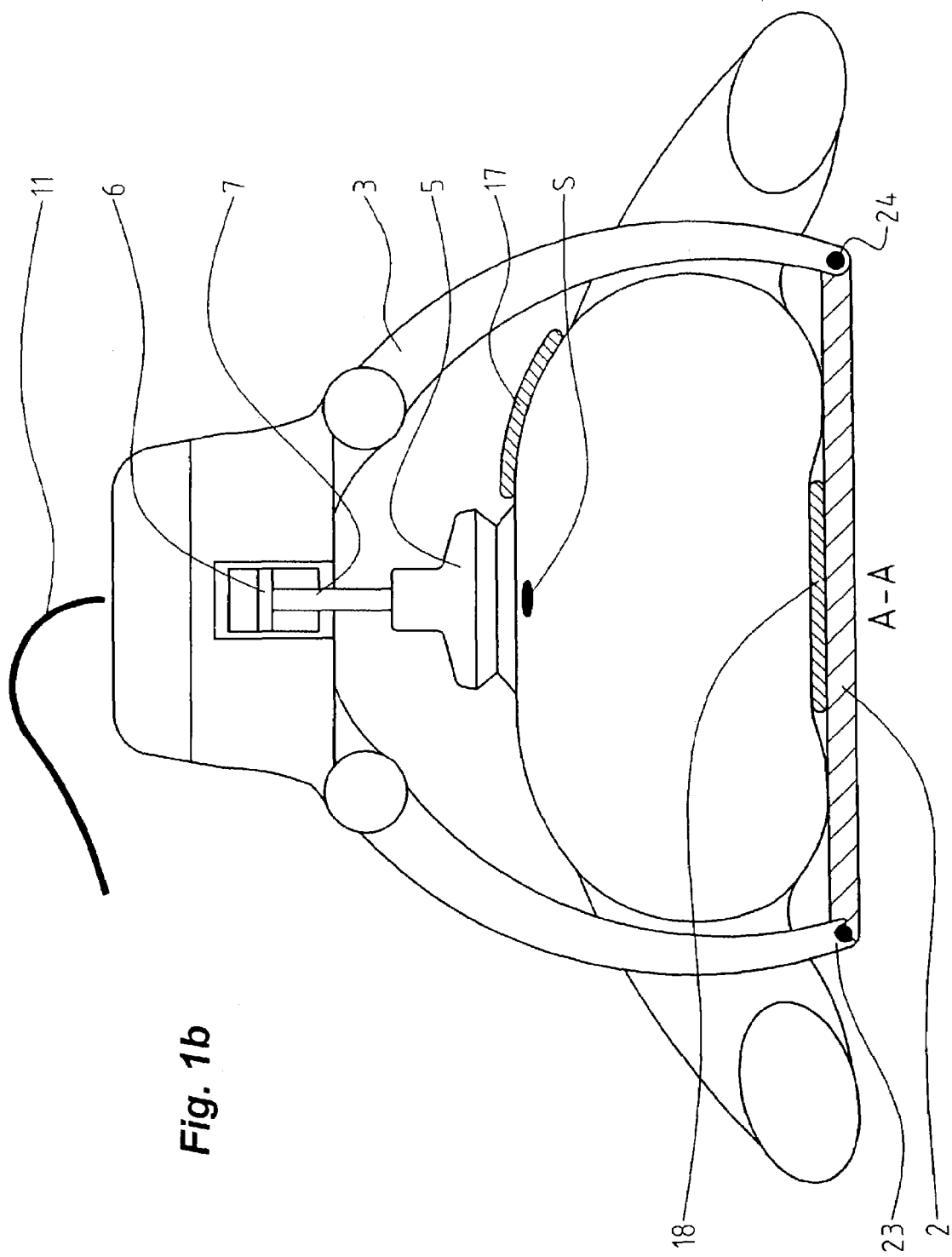

FIGS. 1a and 1b show an exemplary system of apparatus or equipment, which is set up to administer the inventive CPR procedures. The inventive system includes a portable chest compression device or assembly. The compression device may be used for mechanically compressing/decompressing the chest of a subject 1, who is an apparent victim of cardiac arrest. Subject 1 is placed in a supine position on a back plate 2 with sternum S facing upward. Back plate 2 may be provided with a raised neck support 19, which lies under the subject's neck. The neck support may be sufficiently high so that the subject's head falls back and rests against a surface of back plate 2. This inclination of the subject's head places the subject's mouth in a suitable open position for unobstructed or clear access to the airways, for example, for either mouth-to mouth resuscitation or for tracheal intubation.

A pair of hinged leg-like structures extending from yoke 3 mechanically support a pneumatic compression/decompression unit 4 above subject 1. Snap locks 23 and 24 at the free ends of the leg-like structures can be readily attached in the field to back plate 2 to position unit 4 at a proper height above supine subject 1. Unit 4 includes a pneumatic drive cylinder to pneumatically drive a chest contact pad 5 mounted at an end of a rod 7. The other end of rod 7 is attached to a sliding disc 6 that separates chambers 8 and 9 of the pneumatic drive cylinder. Pad 5 is placed in contact with the subject's chest. Suitable adhesives (not shown) may be used to make pad 5 adhere strongly to the subject's chest wall. Upward movement of strongly-adhering pad 5 may then decompress the subject's chest by lifting the chest walls.

In operation, a valve manifold 12 alternately feeds pressurized gas to chambers 8 and 9 of the pneumatic drive cylinder to reciprocate rod 7. Accordingly, contact pad 5 at the end of rod 7 compresses or decompresses the subject's chest. A suitable source, for example, gas cylinder 10, may be used to supply the pressurized gas to valve manifold 12, (e.g., through a flexible reinforced plastic tube 11). A main control unit 13, which includes a microprocessor running on rechargeable batteries, may be used to time the alternating flow of pressurized gas through valve manifold 12 and chambers 8 and 9, and thereby to control or vary the rate at which contact pad 5 compresses or decompresses the subject's chest. Beneficial or suitable compression/decompression rates may, for example, be selected in the range of about 60 cycles/mm to about 200 cycles/mm. Individual CPR systems may be set up for adjustable compression/decompression cycle rates in that range, or in a narrower range (e.g., from about 60 cycles/mm to about 120 or 150 cycles/mm) or in any other suitable range.

The compressed gas that is used to drive the pneumatic drive cylinder may have an oxygen content or composition that also makes it suitable for use as a breathing gas. Having the same gas for either use or purpose mitigates the need to provide or carry two separate gas sources (e.g., cylinder 10) in a portable CPR system. The suitable gas for both purposes may be either air, pure oxygen or a suitable oxygen-inert gas mixture. In any case, the dual-use gas vented from pneumatic cylinder chambers 8 and 9 can be supplied to the subject's airways. Suitable tubing (e.g., flexible tubing 14) may be used to direct the vented gas, for example, to a facial gas mask 15 placed over the subject's mouth and/or nose. Outlet 16 provides an exhaust path for gas fed into mask 15 or expired by the subject.

Suitable gas pressure control circuitry (see e.g., FIG. 5) may be used to regulate the pressure of the breathing gas vented from the pneumatic cylinder chambers 8 and 9. The regulated pressure may be selected to be at a suitable positive pressure, which may be slightly higher than the ambient pressure (e.g., by a few cms of Hg). The capability to control the pressure of the breathing gas may be particularly advantageous when the breathing gas is administered through tracheal intubation (instead of facial mask 15). When the breathing gas is administered through a mask (e.g., mask 15), the breathing gas pressure may be naturally set by the size or diameter of exhaust openings (e.g., outlet 16) or by use of pressure relief valves. The control circuitry of FIG. 5 may then be used optionally to further regulate the breathing gas pressure if necessary or desired.

During administration of CPR, the subject's heart condition may be monitored using ECG or other diagnostic techniques. Suitable contact electrodes 17 and 18 may be used for that purpose (FIGS. 1a and 1b). Electrodes 17 and 18 provide electrical contact to conducting pathways leading to the subject's heart. Front electrode 17 is placed on the subject's chest adjacent to contact pad 5, and rear electrode 18 is placed on the subject's back. The electrodes may be firmly secured to the subject's chest or back using, for example, suitable conducting adhesives. Additionally or alternatively, elastic or spring-loaded elements attached to the yoke 3 may press or hold electrode 17 against the chest. In some variations of the medical equipment, electrode 17 may be integrated into the face or rim of contact pad 5. Similarly, back electrode 18 may be mounted or integrated in back plate 2, so that electrode 18 is in electrical contact with supine subject 1.

Wire or leads 20 and 21 from an electrode control unit 26 are connected, respectively, to electrodes 17 and 18. Electrode control unit 26 may be designed to carry out one or more electrical diagnostic or therapeutic measures (e.g., ECG measurements, defibrillation and pacing). For example, unit 26 may be designed to obtain low voltage ECG measurements to distinguish between asystole and fibrillating heart states, for generating defibrillating bursts of electrical energy, and for generating heart pacing pulses of a suitable frequency or rate. Electrodes 17 and 18 may serve as pacing or defibrillating electrodes in addition to serving as ECG electrodes.

Commercially available defibrillators and pacer units may be suitably adapted for use with control unit 26. Laerdal Medical A/S, of Stavanger, Norway, sells a suitable defibrillator that for example can be adapted for use with control unit 26, under the trade name Heartstart FR2 AED. Similarly, commercially available ECG recorder/analyzers may be integrated in the CPR system. Optionally, electrode control unit 26 may include suitable customized microprocessors or CPU to receive and analyze ECG electrical signals. A rechargeable battery or other suitable power sources may supply electric power to electrode control unit 26. The same rechargeable battery that powers main control unit 13 may be used to supply power to control unit 26. The CPR system also may include an integrated transformer/rectifier as a back up for using electricity from supply mains that may be available at the site of use.

FIGS. 1a and 1b show facial gas mask 15 placed on subject 1 for controlled ventilation. Instead of using a facial gas mask, the subject optionally may be intubated through the trachea for delivery of oxygen or oxygen containing gases directly to the lungs. Any suitable tube may be used for the tracheal intubation. Exemplary endotracheal tubes that may be used are disclosed, for example, in International Patent Publication WO 94/00174. A disclosed endotracheal tube is made from flexible plastic tubing. A flexible tubular tip is attached to the distal end of the plastic tubing. The flexible tubular tip may be made of molded plastic material. An inflatable balloon is attached to a tubular sleeve segment near the distal end of the flexible tubing. A balloon inflating/deflating system is located at or near the proximal end of the flexible tubing. The inflatable balloon and its inflating/deflating system are in fluid communication, for example, through a longitudinal gas channel extending in or along the walls of the flexible tubing.

For CPR intubation, it may be desirable to use an endotracheal tube with a gas channel with a large lumen width or cross section in order to increase gas flow capacity. Desirable lumen widths or cross sections may be up to about 90% of the cross sectional area of the endotracheal tube. Suitable endotracheal tubes are sold, for example, under the trade name "Boussignac adult endotracheal tube" by Laboratories Pharmaceutiques Vygon of Ecouen, France The application of pressurized breathing gas in conjunction with active chest decompression encourages the subject's coronary blood pressure (CPP) to increase. The subject's coronary blood pressure may be beneficially raised or increased over values that may be attained, for example, by manual administration of CPR. In manually administered CPR, the downward force of hand provides only chest compressions. No active decompression of the chest occurs. The coronary blood pressure remains negative (zero to about −5 mm Hg). However, when CPR is administered using automated compressor devices such as the LUCAS™ device, the subject's chest can be actively decompressed. The automated devices decompress by lifting the subject's chest walls to their physiological or natural decompressed state. In response to the active decompression, a vigorous draw or inflow of air or oxygen gas through the trachea into the lungs occurs. The flow of air can be of the order of several liters per minute. For example, while decompressing with a LUCAS™ device, air or oxygen gas inflows of about 15 L/min have been observed. At these gas flow rates corresponding increases in the heart blood pressure (CPP) of about 8 mm Hg positive have been observed.

In the inventive CPR procedures, the flow of pressurized breathing gas can be forced to levels higher than, for example, about 15 L/min. By forcing the flow of additional breathing gas during active chest decompression phases, the subject's coronary blood pressure can be advantageously increased or raised further. For example, by forcing breathing gas at flow rates of about 25 L/min during the periods of active chest decompression, the coronary blood pressure may be raised in some cases by up to about 15 mm Hg.

The breathing gas flow rates are regulated to keep the gas pressure under threshold levels that may cause damage to the lungs. For example, chest compressions using automated devices (e.g., LUCAS™ device) can lead to positive coronary blood pressures of about 15 to 20 mm Hg. The forced flow of additional breathing gas further increases this pressure. Accordingly, the flow of breathing gas may be kept below 20-25 L/min, so that the total pressure does not exceed a lung damage threshold (e.g., 40 mm Hg). Further, the mean positive pressure of breathing gas may be regulated at a suitable value in the range of about 1 mm Hg to about 30 mm Hg, or more specifically in the range from about 8 mm Hg to about 25 mm Hg. A suitable value may, for example, be 20 mm Hg.

During the administration of CPR, electrical stimulation of the heart (e.g., pacing) may be advantageously initiated after some recovery or revival of the subject's heart function in response to the mechanical stimulations. A measure of heart function is the coronary blood pressure. By this measure of recovery, electro-stimulation is administered after a positive CPP is reestablished as described above. A suitable positive CPP value may be chosen as a threshold value after which the electrical stimulation may be initiated. The threshold value may be chosen to be, for example, 10, 15 or 25 mm of Hg. Another indicator of heart function is the accumulation of blood in the left ventricle. Using this indicator of recovery, electrical stimulation of the heart may be initiated only after a sufficient quantity of blood has accumulated in the left ventricle. In the case of an adult subject, an accumulation of 20 ml or more of blood in the left ventricle may be considered to be sufficient. For a child subject, a lower amount of accumulated blood may be considered to be sufficient. Yet another measure of heart recovery or progress in the CPR procedure is the reduction of volume of blood which undesirably pools or collects in the right atrium as a result of asystolia or ventricular fibrillation. Electro-stimulation in the form of pacing may be initiated only after the time-averaged of the volume of blood in the right atrium has been substantially reduced or cleared. Reductions of 50% or so may be used as a threshold or trigger value for initiating pacing.

Electro-stimulation in the form of heart pacing may be particularly desirable or advantageous, for example, in the presence of asystolia or bradycardia. Generally, the administered pacing electrical pulses have a constant frequency or rate (e.g., about 80 beats/min). This pacing rate may be adjusted in proportion to the cycle rate of the concurrently administered chest compression/decompressions. For example, when compression/decompression cycle rates are above 80 cycles per minute, the pacing pulse rate also may be adjusted upwards accordingly.

Figure 2:
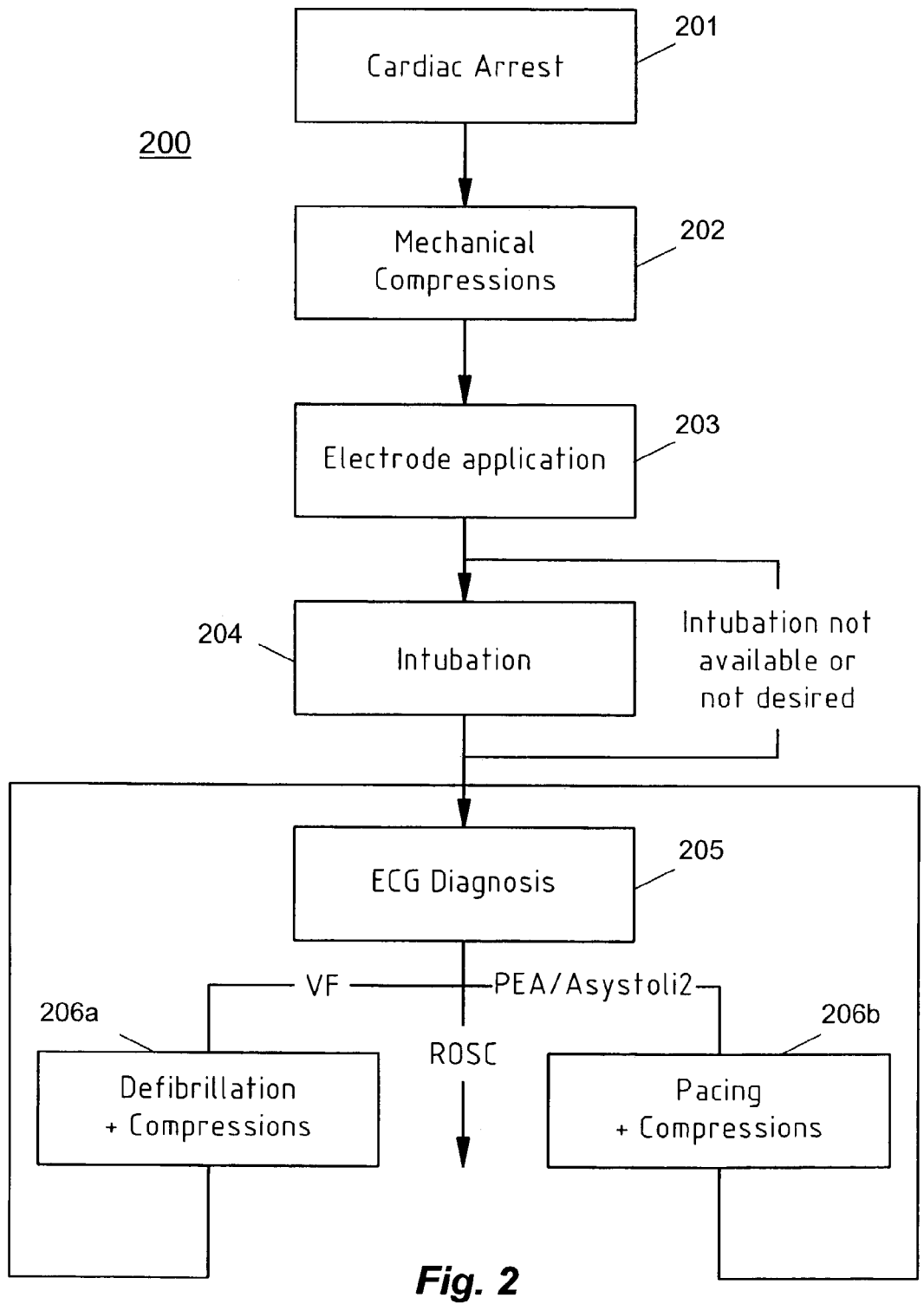
FIG. 2 is a schematic flow chart illustrating some of the exemplary steps performed in administering CPR in accordance with the present invention.

The exemplary steps involved in administering an emergency CPR procedure to revive a subject or victim of cardiac arrest may be understood with reference to a flow diagram 200 shown in FIG. 2. The emergency CPR procedure may be designed to improve or stabilize the subject's condition sufficiently, for example, for transport and further treatment in a hospital. The CPR procedure may be administered using, for example, the system shown in FIGS. 1a and 1b.

In FIG. 2, step 201 indicates that subject 1 is a victim of cardiac arrest. The portable CPR apparatus or system (FIG. 1a) is quickly assembled with supine subject 1 placed or laid on back plate 2. Compressor unit 4/contact pad 5 are aligned with the supine subject's sternum S. At step 202, compressor unit 4 is activated to administer mechanical chest compressions. The mechanical chest compressions may, optionally, be accompanied by intervening periods of active chest decompressions. Even before step 202, as the CPR apparatus is being assembled, manual chest compressions may be initiated by hand to help revive the subject. At step 203, which may be in parallel or sequential to step 202, electrodes 17 and 18 are attached to the subject. The electrodes may. be used to monitor electric activity of the subject's heart. Similarly at parallel or sequential step 204, the subject may be intubated with an endotracheal tube if that is deemed proper or appropriate for ventilation or insufflating breathing gases. The endotracheal tube also may be used to deliver pharmaceutical agents (e.g., an aqueous saline solution of potassium chloride) to the subject in addition to insufflating breathing gasses. Such agents may be cooled to a temperature below room temperature, (e.g., 5° to 10° C. or lower) if desired.

The option to intubate the subject for ventilation may depend on the availability of a skilled person to perform the intubation. Alternatively, the subject may be fitted with a facial gas mask. If neither intubation nor facial gas masks are available or used, manual mouth-to-mouth respiration may be carried out as medically necessary or desired.

At step 205, control unit 26 analyzes electric signals received at electrodes 17 and 18. Control unit 26 may, for example, conduct an ECG diagnosis to evaluate the state of the subject's heart. The diagnosed states may, for example, include asystolia (i.e., electro mechanical dissociation (EMD)), ventricular fibrillation (VF), pulseless electric activity (PEA), or an electrically "normal" or satisfactory state that does not require defibrillation or pacing therapy.

The course of the therapeutic CPR procedure may be suitably modified according to the results of the evaluation. For example, if the diagnosed state is ventricular fibrillation, then at step 206a defibrillating electrical shock or energy may be administered to subject 1 through electrodes 17 and 18. If the diagnosed state is PEA or asystolia, then at alternative step 206b, electrical pacing pulses are administered through electrodes 17 and 18. During either of steps 206a or 206b, the sequence of mechanical chest compressions (step 202) may be concurrently continued. The sequence of mechanical chest compressions may optionally include intervening active decompressions of the chest.

Control unit 26 may be used to reevaluate the state of the subject's heart intermittently or continuously during the CPR procedures. FIG. 2 shows, for example, ECG diagnosis (step 205) repeated after either of steps 206a or 206b. This reevaluation may show the progress or effect of the CPR treatment and thus guide the course of further therapeutic measures.

When ventricular fibrillation is diagnosed or indicated at step 205, electrical defibrillation at step 206a and the accompanying chest compressions (with or without intervening active decompressions) may be prolonged or continued as long as desired or necessary for good therapy. Step 206a may be continued, for example, until the return of spontaneous circulation (ROSC) is observed. After ROSC is observed, the electrical defibrillation may be discontinued. The discontinued electrical defibrillation may be then replaced with electrical pacing of the heart (e.g., at step 206b).

Similarly when asystolia or PEA are diagnosed or indicated at step 205, then at step 206b the electrical pacing of the heart may be continued at least until ROSC is observed. In many instances, electrical pacing may be continued for long time periods after ROSC is observed. The electrical pacing may be continued, for example, during the transport of the subject to a hospital for further therapy or treatment.

Figure 3:
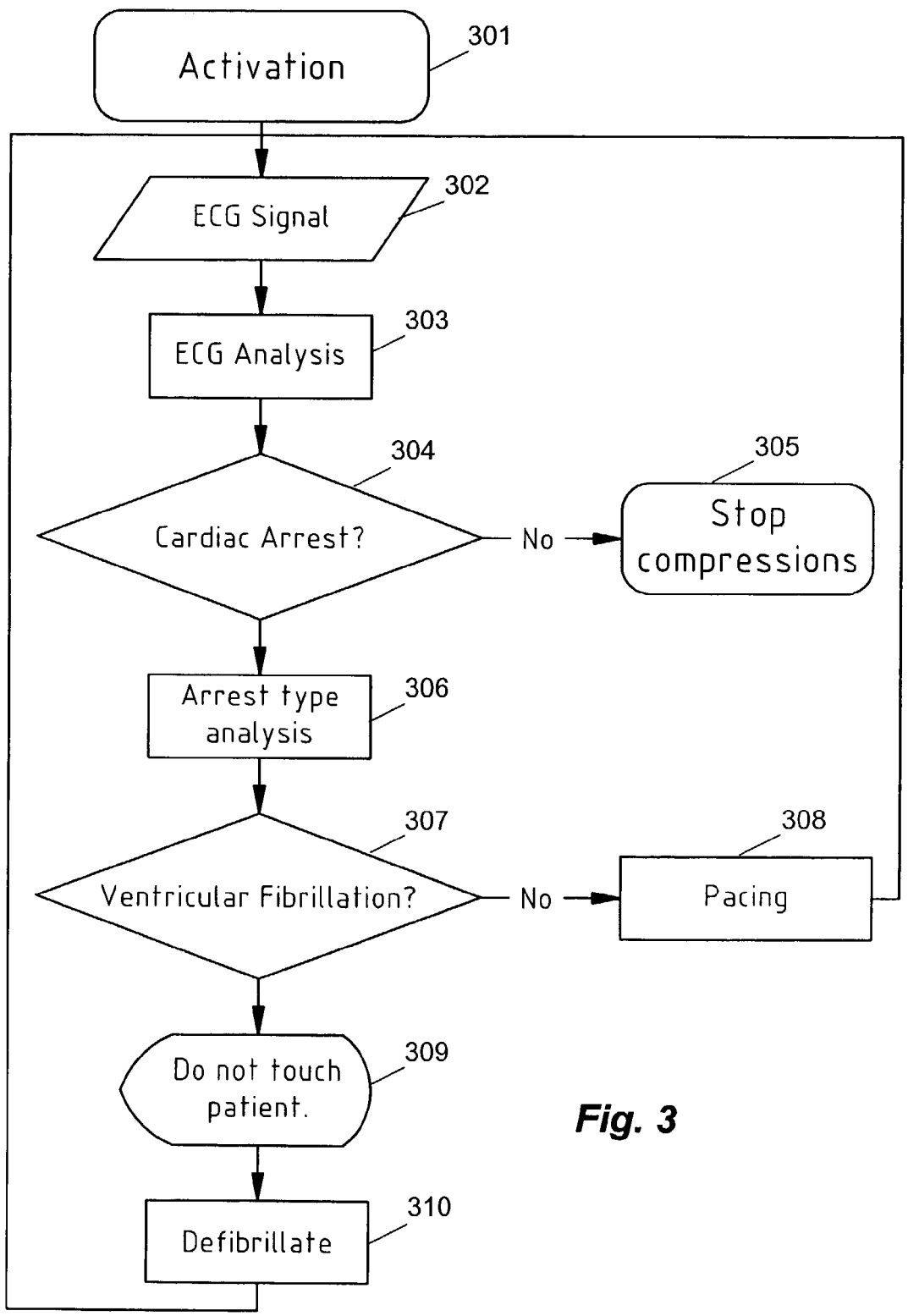
FIG. 3 is a schematic flow chart illustrating some of the exemplary steps in an electrocardiogram (ECG) analysis or diagnosis of a subject that lead to different therapeutic choices in accordance with the present invention.

FIG. 3 outlines, for example, an exemplary sequence of therapeutic decisions 300 that may be involved in administering the inventive CPR procedures to a subject who is an apparent victim of cardiac arrest. It will be understood that the steps shown in FIG. 3 are only illustrative and that they may be performed in any suitable order. In practice, some of the steps may be omitted, and additional steps that are not shown in FIG. 3 may be included.

Block 301 denotes the activation of a compression device to administer mechanical chest compressions/decompressions to the subject who is an apparent victim of cardiac arrest. Blocks 302 and 303 respectively denote the collection and analysis of ECG signals from the subject.

A first therapeutic decision 304 pivots on an assessment at block 303 of whether the subject's heart has stopped beating (i.e. actual cardiac arrest) or is beating faintly. In both cases the subject's body temperature can be several degrees below the normal body temperature. However, if the ECG analysis at block 303 detects a pulse even though feeble or faint, then there is no cardiac arrest. When the heart is beating feebly or faintly, some CPR measures such as chest compressions may not be indicated. Accordingly, at block 305 mechanical compression/decompression are ceased.

If the ECG analysis at block 302 detects no pulse then cardiac arrest is confirmed. Next block 306 denotes further ECG or other analysis to determine the nature or type of cardiac arrest. This analysis may evaluate the electrical state of the heart to determine if ventricular fibrillation, PEA or other heart conditions are present.

A second therapeutic decision 307 may depend on the result of the analysis at block 306. If, for example, ECG analysis at block 306 shows that ventricular fibrillation is absent, then electrical pacing of the subject's heart may commence at block 308. If the ECG analysis at block 306 instead shows signal patterns characteristic of ventricular fibrillation, then at block 310 the subject's heart may be defibrillated.

During defibrillation by application of electrical energy, the subject must be electrically isolated from other persons (e.g., to avoid energy leakage or shock to the other persons). The CPR apparatus may include suitable alarms to indicate the imminence of defibrillation. Block 309 denotes an alarm or message to other persons to cease touching the subject in preparation for defibrillation at block 310. After defibrillation at block 310 and suitable reevaluation, another decision (not shown) may be made to administer pacing electrical pulses, for example, at block 308.

The inventive CPR system may be configured to automatically execute a sequence of one or more therapeutic decisions, for example, as in sequence 300. The automatic execution of therapeutic decisions may advantageously allow persons with little or no medical training to use the system to administer CPR in emergencies.

Additionally, the CPR system also may be configured to allow for human intervention or guidance in every therapeutic decision. Control unit 26 and/or other equipment in the system may be provided with suitable input/output arrangements. Output displays may show, for example, every diagnostic analysis or result. Control unit 26 and/or other equipment in the system also may be provided with input mechanisms by which an operator can, for example, override automated decisions and/or initiate a specifically tailored course of therapeutic measures.

Figure 4:
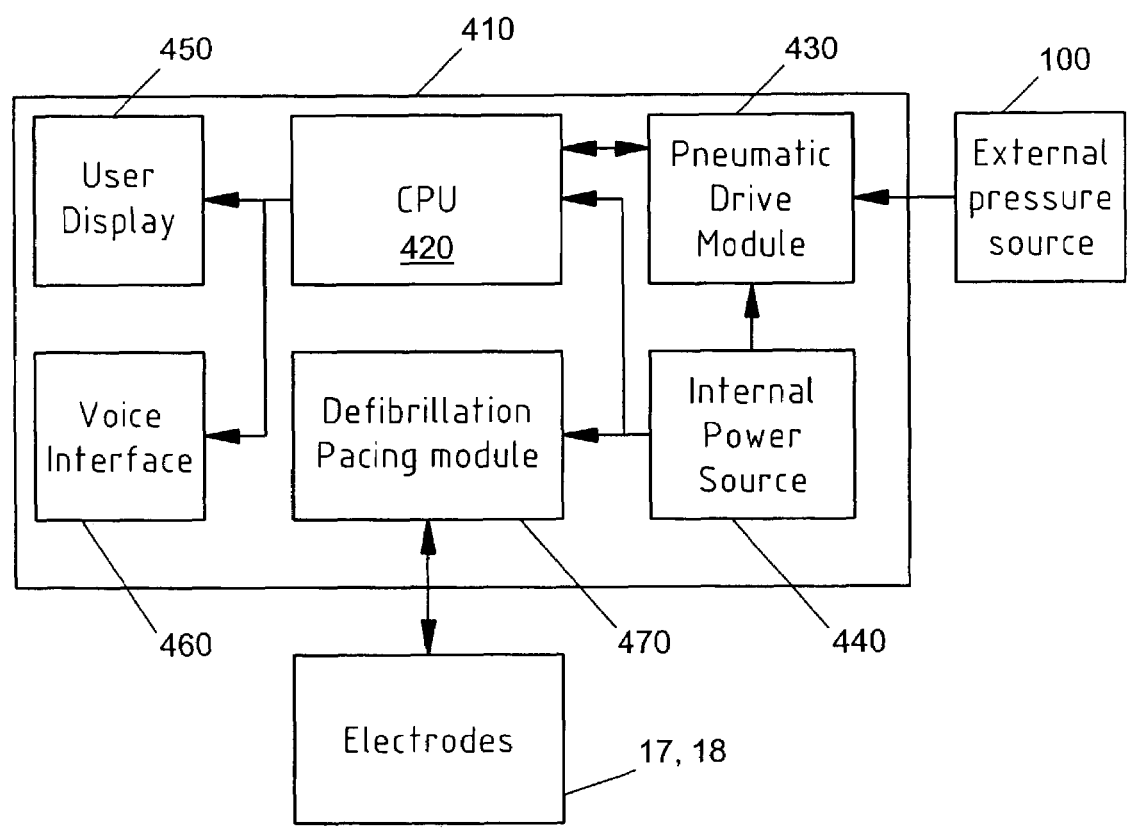
FIG. 4 is a schematic block diagram illustrating the relation between various components of a control unit of a CPR system in accordance with the present invention.

FIG. 4 shows, for example, an illustrative configuration of the various functional blocks or components of control unit 410 of an automated CPR system. Microprocessor (CPU) 420 controls the functioning of control unit 410. CPU 420 may include conventional memory for data storage and for storing computer programs or software (not shown). The stored data may include, for example, a catalog or library of ECG signals of the various types of cardiac arrest. The computer programs may include software for digitizing electrode signals, and software for comparing them with cataloged data on the various types of cardiac arrest or other heart activity. The computer programs may also include software for controlling pneumatic drive module 430 and/or other modules or equipment that may be used in the CPR system. CPU 420 may be powered by an internal power source 440, which can be a rechargeable battery. CPU 420 may be linked to an output display 450 and to an optional voice interface 460. Display 450 may, for example, be a conventional CRT, LCD or plasma screen. Display 450 may be used for displaying alphanumeric or graphical data and messages such as ECG signals or other information. Voice interface 460 may be used to provide audible information. The audible information may include, for example, instructions to replace the breathing gas source when it is running low or warnings to avoid contact with the subject during defibrillation.

Control unit 410 further includes defibrillator/pacer module 470. Module 470 may include a suitable voltage transformer to provide electrical signals having appropriate defibrillating or pacing voltages and currents to electrodes 17 and 18. Module 470 may include suitable built-in software and hardware for ECG analysis. Module 470 can be a commercially available defibrillator/pacer, which is suitably adapted for use in control unit 410. A defibrillator/pacer unit suitable for this purpose may, for example, be similar to those sold previously under the trade name "Cardio-Aid Model 200 Defibrillator" by Artema Medical AB of Stockholm, Sweden (which was acquired in December 2001 by Cardiac Science, Inc., U.S.A.). Internal power source 440 may supply electric power to module 470 and also to pneumatic drive module 430.

Figure 5:
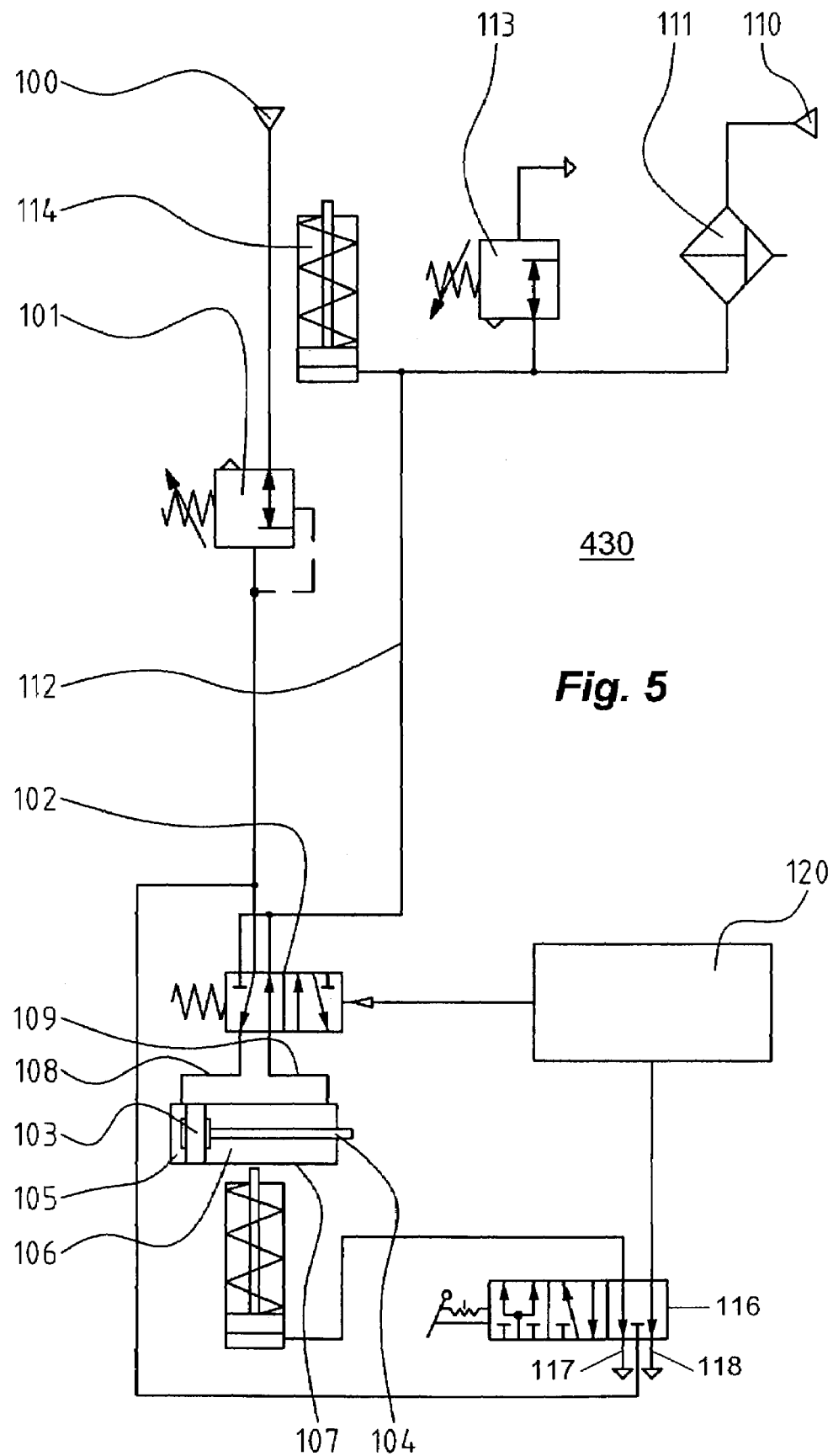
FIG. 5 is a schematic representation of the pneumatic circuitry for driving a compressor unit of a CPR system. The pneumatic circuitry includes provisions for supplying vented gas under pressure to a subject's airways in accordance with the present invention.

An exemplary pneumatic drive module 430 is shown in FIG. 5. An external gas supply 100 is connected to a pressure regulator/valve 101 in module 430. Gas supply 100 may, for example, be a breathing-grade oxygen gas flask. The oxygen gas flask may contain gas under pressure. Pressure regulator/ valve 101 may be used to reduce and regulate the downstream pressure of the gas flowing into a valve manifold 102. Control unit 120 (e.g., CPU 420) may electronically control these valves. Valve manifold 102 is designed to direct pressurized oxygen gas into gas lines 108 and 109 that respectively lead to chambers 105 and 106 in a pneumatic cylinder 107. In operation, valve manifold 102 alternately feeds pressurized oxygen gas to chambers 105 and 106 to drive separating piston 103 reciprocally in cylinder 107. A connecting shaft 104 couples the reciprocating movement of piston 103 to that of a chest contact pad (not shown).

The gases that are alternately fed into chambers of 105 and 106, on return, are vented by valve manifold 102 into gas line 112. Gas line 112 leads to an exhaust port 110. In use, exhaust port 110 may be connected to a facial gas mask or an endotracheal tube so that the vented gases can be used as a breathing gas in the CPR procedures. The pressure and flow of the vented gases through exhaust port 110 is suitably controlled or regulated for use as a breathing gas. For example, conventional gas flow control devices such as a flow attenuator 114, a safety pressure release valve 113, and a ballast or reservoir 111 may be placed in line 112 to regulate the outflow of breathing gas through exhaust port 110. Additional or alternate gas flow circuitry (not shown) also may be used to further regulate the pressure of the breathing gas through exhaust port 110.

The CPR system may be configured (e.g., by suitably programming CPU 420) to carry out one or more therapeutic steps or measures in co-ordinated time sequences. The reciprocating times and travel distances of the chest contact pad may be programmably adjusted so that the subject's chest is in either a fully compressed state or a fully decompressed state during most of a compression/decompression cycle. Controlling the speed at which compressed gases are switched between opposing chambers of the pneumatic drive cylinder may set the transition times between the two states. The transition times may be suitably set so that they are a small fraction of the period of a compression/decompression cycle. The transition times may, for example, be in the range from about a sixth of a cycle to about a tenth of a cycle.

Figure 6:
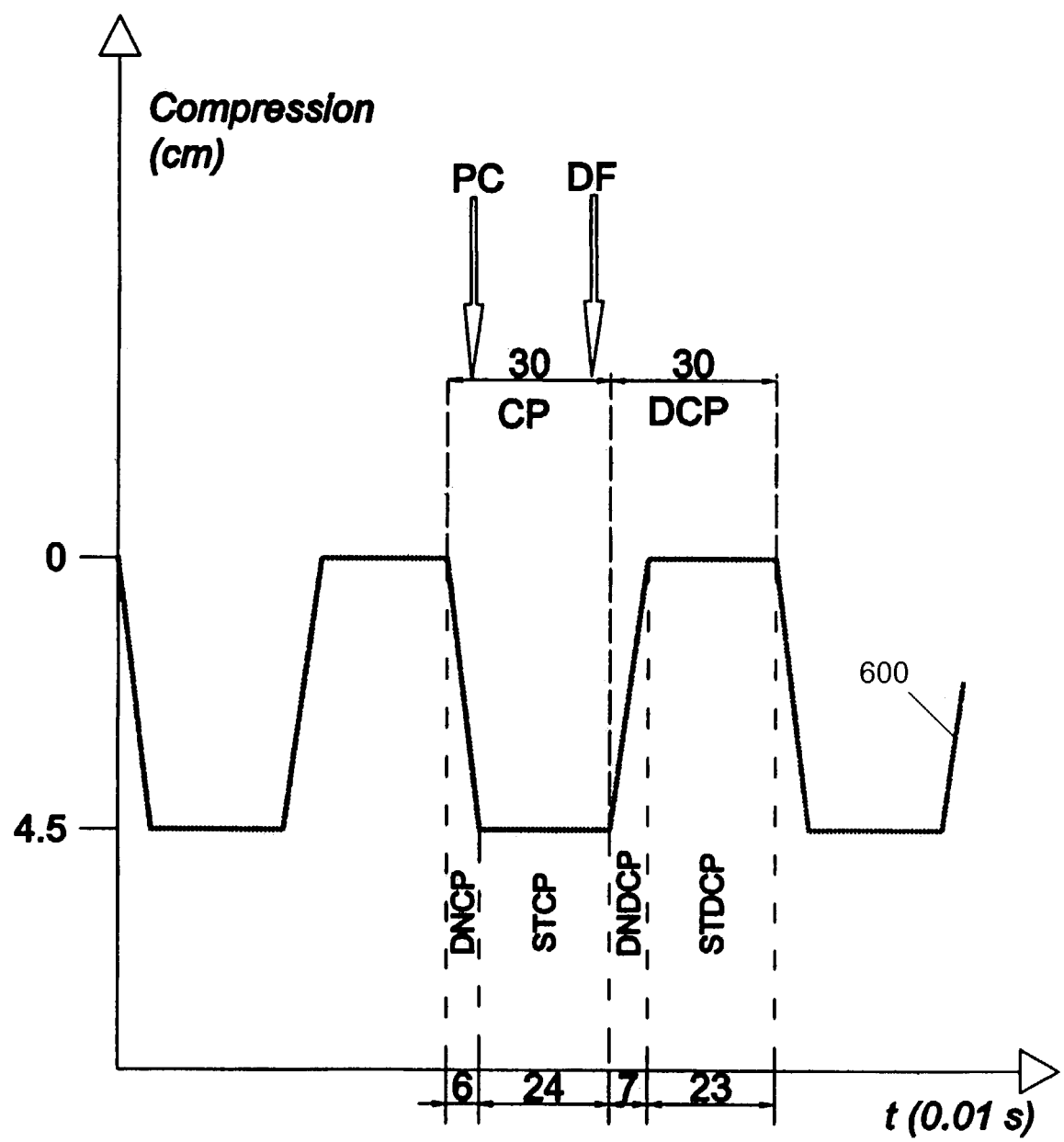
FIG. 6 is a schematic time trace illustrating the chest compression/decompression cycles and the co-ordination or synchronization of electro stimulation in accordance with the present invention.

FIG. 6 shows, for example, an exemplary trace 600, which graphically represents the chest compression depths as a function of time over a few compression/decompression cycles. The time period of a compression/decompression cycle may, for example, be about 0.60 seconds. Each compression/decompression cycle includes a compression half-cycle or phase CP and a decompression half-cycle or phase DCP.

Each compression phase CP is about 0.30 seconds long and includes a dynamic portion DNCP and a static portion STCP. Similarly, each decompression phase DCP is about 0.30 seconds long and includes a dynamic portion DNDCP and a static portion STDCP. The static portions STCP and STDCP respectively represent the fully compressed and decompressed depths of the chest (e.g., depths of about 4.5 and zero centimeters, respectively). Further these static portions (which, for example, are respectively 0.24 and 0.23 seconds long) extend over most of the respective phases CP and DCP. The dynamic portions DNCP and DNDCP respectively represent the rapid transition from a fully decompressed state (STDCP) to a fully compressed state (STCP) and vice versa. The dynamic portions DNCP and DNDCP are small fractions of the compression/decompression cycle. DNCP and DNDCP may, for example, respectively be 0.06 and 0.07 seconds long.

The relatively long fully compressed/decompressed portions (STCP and STDCP) with abrupt or rapid intervening transitions (DNCP and DNDCP) give trace 600 a trapezoidal wave shape. This trapezoidal wave shape of mechanical chest compressions/decompressions is administered to the subject while the subject is being induced to expire and inspire against pressurized breathing gas to increase the blood pressure or CPP. CPU 470 may be programmed to initiate electrical stimulation of the heart after a threshold CPP (which, for example, may be set at 10, 15, or 25 mm Hg) is reached. CPU 470 may be programmed to initiate defibrillating electro-stimulation during the last third of the static portion of the compression phase STCP. In FIG. 6 arrow DF indicates the start of defibrillation.

Similarly, CPU 470 may be programmed to initiate pacing electro-stimulation (PC) within the time interval from the start of a compression phase CP up to the start of the next decompression phase DCP. In FIG. 6 arrow PC indicates the start of pacing. In some cases, CPU 470 may be programmed to initiate pacing during the second half of the dynamic portion of the compression phase (DNCP) and the first half of the static compression phase (STCP). In some instances pacing may be initiated within 0.10 to 0.15 seconds from the end of a dynamic compression phase (DNCP).

The exclusive time periods in which only the initial mechanical compressions/decompressions are administered (e.g., prior to the co-application of electro-stimulation after increased CPP is seen) typically can be up to 180 seconds long. This exclusive time period may vary according to the assessments of the nature or type of cardiac arrest and/or the measurements of CPP. For example, in the case of short episodes of asystolia (e.g., lasting from 10 seconds to 50 seconds), the exclusive time period may be about 30 seconds or more. In the case of longer episodes of asystolia (e.g., lasting 2 minutes or more), the exclusive time period may be as long as 5 minutes or more.

The CPR system also may have suitable pneumatic drive power management features (e.g., FIG. 5) that can be used to adjust the force used to compress the subject's chest. The drive power may be adjusted to regulate the chest compression depths. Adjustment of the pneumatic drive power to maintain chest compression depths may be necessary or desirable, for example, in response to the changing chest resistance as the subject's heart function revives. Empirical observations show, for example, that the force required to compress the chest to a certain depth (e.g., 3.0 to 4.5 cms) decreases with time into the CPR administration. About 25 percent less force may be required after about 20 to 60 seconds from the start of the chest compressions.

Desired compression depths (e.g., as in trapezoidal wave shape 600) may be maintained in time by monitoring the chest resistance intermittently, and accordingly adjusting the pneumatic cylinder drive power. Conventional pneumatic circuit elements (e.g., elements 115, 116 and 117 of FIG. 5) may, for example, be used to monitor the chest resistance and to provide stops to limit the travel distances of shaft 104. Adjustments to the pneumatic cylinder drive power may be made by suitably adjusting pressure regulator 101 (FIG. 5) to regulate the flow and pressure of the driving/breathing gas. Such monitoring and regulation may maintain, for example, exemplary trapezoidal wave shape 600 of the compressions/decompression cycles over the entire course of CPR treatment.

Examples of CPR Treatment:

1. A 73-year old woman collapsed while attending a concert (at time zero minutes). The woman had a history of a coronary bypass surgery (5 years ago) and a myocardial infarction (3 years ago). A physician who was also present at the concert found no palpable pulse, and began manual CPR immediately (15 chest compressions and 2 mouth-to-mouth in-blowings per minute). A paramedic ambulance with a portable CPR device (LUCAS™) arrived at 6 minutes. The CPR device was assembled and used to administer mechanical chest compressions to the woman. At 7.5 min ECG measurements indicated ventricular fibrillation. The woman was then intubated through her mouth with a tracheal tube (Boussignac). Oxygen gas obtained from the CPR device was insufflated through the tracheal tube at the rate of 15 liters/min. At 8.5 minutes, a pulse oxymeter was connected to the woman's fingertip. Pulse oxygen saturation readings of 100% were obtained. The woman's skin had regained a reddish appearance indicating good skin circulation. Good palpable pulses were felt in the neck and groin (in the carotid artery and femoral artery, respectively). Ventricular fibrillation was noted as becoming increasingly coarse (on an ECG display screen of the CPR device). At 9 minutes a defibrillation shock of 360 Joules was administered during a chest compression phase. In response, the woman's heart became asystolic, but about 10 seconds later a sinus rhythm with a frequency of 60 beats/min was seen. Mechanical chest compressions were continued until the sinus rhythm frequency had risen to 90 beats/min at 12 minutes. The compressor device was then turned off. Within a minute thereafter, the woman's pulse weakened and pulse oxymetric readings decreased from about 100% to about 70%. Mechanical chest compressions were reinitiated. The woman was placed on a stretcher (along with the CPR device) and transported in the ambulance to a hospital. During transport, mechanical chest compressions and oxygen insufflations were continued. On arrival at the hospital's emergency room at about 25 minutes, the pulse oxymetric saturation had increased to 100%. Minimally invasive probes were inserted in the woman's' vasculature to sample blood for gas level measurements. In particular, an arterial needle was inserted in the radial artery, and a central venous catheter was advanced into the external jugular vein using Seldinger's technique. Blood gas measurements showed arterial blood oxygenation levels were superior to normal ($PaO_2$=49, pH 7.45, $PaCO_2$=3.5, Base excess −1). The compressor device was then turned off. The woman's readings showed a sinus rhythm with a frequency of 90 beats/min, and a blood pressure of 110/70 with a mean of 90. The woman was placed under close observation for 24 hours in an intensive care unit. No signs of myocardial infarction were observed. The woman was stable and fully conscious throughout. After a week of normal hospital care, she was released and sent home. A one-month follow-up checkup showed she was fully recovered.

2. A 36-year old man showing no signs of life was found early in the morning in a park in freezing temperatures (−1° C.). A paramedic ambulance arrived at about 5 minutes. Neither pulse nor respiration was detected. The body temperature was 22° C. ECG measurements revealed extreme bradycardia at 2-3 beats per minute. An emergency call was placed to a physician. The physician rushed from home to the site with a portable CPR device (LUCAS™). After observation of the man's small or constricted eye pupils, the CPR device was assembled and mechanical chest compressions begun. The man then was intubated with a Boussignac endotracheal tube for ventilation. The Boussignac tube was connected to an oxygen exhaust line of the CPR device for continuous insufflations of oxygen. Low voltage ECG indicated development of a sinus rhythm with a frequency of 3 to 5 beats/min. Good palpable pulses were felt in the carotid artery. The man was transported in the working CPR device directly to a hospital operating theatre. A heart-lung machine was connected through the femoral blood vessels. The body temperature was slowly warmed up to 32° C. At this stage, the man's heart was beating vigorously at 70 beats per min, producing a pressure of 110/60. After being weaned from the heart-lung machine, the man was taken to an intensive care unit. There he was allowed to warm up spontaneously to normothermic temperatures over the next 6 hours. After one week, he was found to be in good condition for release from the hospital.

3. A 48-year old man collapsed in his office at 10 a.m. No resuscitation was attempted. An emergency cardiac-response paramedic team was summoned, and they arrived by ambulance at 4 minutes. No palpable pulse was felt in the carotid artery. A pale spot on the skin after a finger-press indicated circulatory arrest. The man was quickly placed in a portable CPR device (LUCAS™) device. Mechanical chest compressions were initiated within about 30 sec. ECG showed asystolia. The man's cheeks were lifted to clear his airways and keep them unobstructed. A Rubens bag with a face mask was used to ventilate the man. An oxygen exhaust channel of the CPR device was connected to the Rubens bag. Oxygen was insufflated at about 15 L/min. A pressure safety valve on the Rubens bag kept the gas pressure in the bag below 30 cm of water (about 1 psi). In this manner, the man was ventilated with 100% oxygen gas while chest compressions were administered at about 100 cycles/mm. A pulse oxymeter placed on the fingertip showed good pulses with 98% oxygen saturation. The flow rate of oxygen gas was further increased. A responsive increase in the oxygen saturation to 100% was observed. However, ECG indicated an asystolic heart state. The CPR device's pacemaker was activated, and heart-pacing pulses were applied at the end of the decompression phase in each chest compression/decompression cycle. Palpable pulses in the carotid artery were felt. The man's eye pupils, which were dilated at the start of resuscitation, began to constrict. The mechanical chest compressions were discontinued, and only the heart pacing was continued. But then the man's pulse started to weaken and the oxygen saturation readings began to fall. In response, mechanical chest compressions were reinitiated, which promptly returned the oxygen saturation to 100%.

A physician and nurse arrived at about 7 minutes, by which time the man was a well-oxygenated and well-circulated. The CPR device was administering chest compressions at 100 cycles/per min and applying heart pacing pulses with a frequency of 100 beats/min.

Interrupting (stopping) the chest compressions lead to an immediate fall in oxygen saturation reading. Accordingly, the chest compressions were resumed. Ventilation through the Ruben bag or mask was stopped. Instead the man was intubated with a Boussignac endotracheal tube for ventilation. Oxygen gases vented from the CPR device's pneumatic drive cylinder were insufflated at a flow rate of about 25 L/min. The frequency of chest compressions was increased to 120 per minute while maintaining the pacing pulses at a frequency of 100 beats/mm. After a further 5 minutes, pacing was stopped, and the chest compression frequency was reduced to 80 per minute. The development of a sinus rhythm with a frequency of about 65 per minute was observed. An arterial needle was placed in the radial artery and the chest compressions were discontinued. An arterial blood pressure of 115/80 was recorded. The patient was put on a stretcher along with the mounted CPR device for transport to a hospital. Chest compressions were stopped but ECG monitoring continued.

During the transport to the hospital, an extreme bradycardia was observed. Systolic blood pressures fell below 60. Chest compressions at 100 cycles/min were resumed and the application of pacing pulses was renewed. On arrival at the hospital both the chest compressions and pacing were again stopped. ECG showed a grade III heart block and a pulse frequency of about 35. Chest compressions and pacing (both at 100 cycles/min) were immediately re-started. The arterial pressure quickly rose to 120/80 and full oxygen saturation was obtained.

The man was taken to the operating theatre where a permanent pacemaker was transvenously implanted in the right ventricle with one electrode in the right atrium. During the implantation of the internal or permanent pacemaker electrodes, the portable CPR device continued to administer external chest compressions and pacing pulses (both at 100 cycles/min). After the permanent pacemaker had been implanted, the chest compressions and the application of external pacing pulses was stopped. Instead, the implanted pacemaker was used to pace the heart. The man's condition was stable with a pacemaker rhythm of 100 beats per minute. He was next taken to an intensive care unit and put on a ventilator support for a day. On extubation he was fully awake but had complete amnesia regarding his collapse and subsequent treatment. After a week of recuperation he was released from the hospital in good condition.

One skilled in the art will appreciate that the present invention can be practiced by other than the described embodiments, which are presented for purposes of illustration and not of limitation.

The invention claimed is:

1. A method for cardiopulmonary resuscitation of a person, comprising:
    providing a breathing gas under positive pressure to the airways of the person;
    mechanically stimulating the person's heart using a pneumatic drive unit to reciprocate a rod for compressing and decompressing the person's chest while inducing the person to inspire and expire against the positive pressure of the breathing gas for at least a period of time until a positive coronary perfusion pressure develops; and
    electrically stimulating the heart once the positive coronary perfusion pressure exceeds a threshold pressure, wherein the pneumatic drive unit is driven by a gas that is recycled for use as the breathing gas.

2. The method of claim 1 wherein the threshold value of the coronary perfusion pressure is selected in the range of about 10 mm Hg to about 25 mm Hg.

3. The method of claim 1, wherein the breathing gas is cooled to a temperature of about at least 5° C. below the ambient temperature.

4. The method of claim 1, wherein the positive pressure of breathing gas maintained in the person's lungs is in the range from about from 1 mm Hg to 30 mm Hg.

5. The method of claim 1 further comprising administering medications using the breathing gas as a carrier.

6. The method of claim 1 wherein mechanically stimulating the person's heart comprises using the drive unit to compress the person's chest to a compression depth, further comprising adjusting the drive unit to control the compression depth in response to changes in the chest resistance during the course of cardiopulmonary resuscitation of the person.

7. The method of claim 1 wherein mechanically stimulating the person's heart comprises externally compressing and decompressing the person's chest.

8. The method of claim 7, wherein externally compressing and decompressing the person's chest comprises compressing the person's chest at a rate between about 60 cycles/mm to about 200 cycles/mm.

9. The method of claim 7, wherein externally compressing and decompressing the person's chest further comprises:
    in cycles, compressing the chest to a fully compressed state in a compression phase of a cycle; and
    decompressing the person's chest to a fully decompressed state in a decompression phase of the cycle, and wherein the transition times in cycling between the two states are no more than a fraction of a cycle period.

10. The method of claim 7, wherein the positive pressure of breathing gas is maintained in the person's lungs while the person's chest is decompressed.

11. The method of claim 9 wherein the fully compressed state corresponds to a static portion of the compression phase, and wherein electrically stimulating the heart according to claim 1 further comprises initiating defibrillation within the last third of the static portion of the compression phase.

12. The method of claim 9 wherein electrically stimulating the heart according to claim 1 comprises initiating pacing the heart in a time interval in between the start of the compression phase and the start of the decompression phase.

13. The method of claim 12, wherein a transition from a decompressed state to the fully compressed state corresponds to a dynamic portion of the compression phase, and wherein the time interval is within 0.10 to 0.15 seconds before the end of the dynamic compression phase.

14. The method of claim 1 wherein the period of time for which the person's heart is mechanically stimulated is adjusted in proportion to the duration of asystolia undergone by the person's heart.

15. The method of claim 1 further comprising:
    assessing the state of the person's heart; and
    accordingly selecting a method for electrically stimulating the heart.

16. The method of claim 1 wherein the person's heart is concurrently both mechanically stimulated and electrically stimulated.

17. The method of claim 1 wherein the person's heart is alternately mechanically stimulated and electrically stimulated.

18. The method of claim 1 wherein electrically stimulating the person's heart comprises defibrillation.

19. The method of claim 1 wherein electrically stimulating the person's heart comprises applying heart pacing pulses.

20. The method of claim 19 wherein a pacing pulse rate is proportional to a cycle rate of concurrently administered chest compression/decompression cycles.

21. The method of claim 20, wherein the pacing pulse rate is substantially flat when the cycle rate is below about 80 cycles/mm and then increases substantially linearly with the cycle rate when the cycle rate exceeds about 80 cycles/min.

22. The method of claim 1, wherein electrically stimulating the heart further comprises initiating electric stimulation after a quantity of blood is accumulated in the left ventricle of the person.

23. The method of claim 1, wherein electrically stimulating the heart further comprises initiating electric stimulation after a time average-mean volume of blood pooled in the right atrium of the person has been substantially reduced by the mechanical stimulation of the heart.

24. The method of claim 1 wherein electrically stimulating the person's heart comprises using a stimulation method selected based on an evaluation of the person's heart condition during the course of the cardiopulmonary resuscitation.

25. The method of claim 24 wherein the evaluation comprises ECG analysis.

26. A system for administering steps in a course of cardiopulmonary resuscitation to a person, comprising:
   a chest compression device for administering mechanical stimulation to the person's heart using a pneumatic drive unit to reciprocate a rod for compressing and decompressing the person's chest;
   a module for administering electric stimulation to the heart;
   a control unit for coordinating the administration of mechanical and electric stimulation to the heart over the course of the cardiopulmonary resuscitation; and
   means for supplying pressurized breathing gas to the person's lungs during the course of the cardiopulmonary resuscitation, wherein the pneumatic drive unit operates on a gas, and wherein the means for supplying the pressurized breathing gas recycles the gas that is used to operate the pneumatic drive unit.

27. The system of claim 26 wherein the control unit further comprises an analysis unit for assessing the state of the person's heart during the course of the cardiopulmonary resuscitation.

28. The system of claim 27 wherein the analysis unit is an electrocardiogram recorder/analyzer.

29. The system of claim 27 wherein the control unit comprises a program for automatically modifying steps in the course of the cardiopulmonary resuscitation in response to assessments made by the analysis unit.

30. The system of claim 26 wherein the means for supplying pressurized breathing gas to the person's lungs comprises means for disposing medication in the breathing gas for administration to the person.

31. A method for administering a course of cardiopulmonary resuscitation to a person using the system of claim 26, comprising;
   assessing an improvement in heart function by the administration of mechanical stimulation to the heart; and
   administering electric stimulation to the person's heart after the improvement in heart function crosses a threshold.

32. The method of claim 31 wherein assessing the improvement in heart function comprises evaluating at least one parameter from the group of parameters that includes:
   a percent reduction in the volume of blood pooled in the right atrium of the person;
   a quantity of blood accumulated in the left ventricle of the person; and
   a coronary perfusion pressure.

33. The method of claim 31 further comprising applying breathing gas under pressure to the airways of the person during mechanical stimulation of the heart for raising the coronary perfusion pressure.

34. A non-invasive method of re-establishing adequate circulation in a person under cardiac arrest comprising:
   providing a breathing gas under positive pressure to the airways of said person;
   mechanically stimulating the heart of said person using a pneumatic drive unit to reciprocate a rod for repeatedly compressing and decompressing the person's chest at a rate from 60 cycles per minute to 200 cycles per minute, while making the person inspire and expire against the positive pressure of the breathing gas for a period of time sufficient to establish a positive coronary perfusion pressure;
   consecutively to the start of the provision of said breathing gas and said compression and decompression, providing electro-stimulation, with the proviso that the electro-stimulation is provided only consecutively to the establishment of a positive coronary blood pressure, while continuing with mechanical stimulation and provision of said positive pressure gas; and
   optionally repeating the steps of exclusive mechanical stimulation and mechanical stimulation concomitant with electro-stimulation, wherein the pneumatic drive unit is driven by the breathing gas, and wherein the breathing gas inspired by the person during said mechanical stimulation is substantially breathing gas consumed in driving said pneumatic drive unit.

35. The method of claim 34, wherein the compression and decompression is administered so that the time from going from a fully compressed state to a fully decompressed state and vice-versa extends over a period corresponding to from about a sixth of a compression/decompression cycle to about a tenth of a compression/decompression cycle.

36. The method of claim 34, wherein a positive pressure of breathing gas is maintained in the lung of the person during decompression.

37. The method of claim 36, wherein the arithmetic mean of said positive pressure of breathing gas in the lung over the decompression phase (DC) of a breathing cycle is from 1 mm Hg to 30 mm Hg.

38. The method of claim 34, wherein the provision of electro-stimulation is started once a positive coronary perfusion pressure of 10 mm Hg has been obtained.

39. The method of claim 34, wherein the provision of electro-stimulation is started once a positive perfusion pressure of 15 mm Hg or more has been obtained.

40. The method of claim 34, wherein defibrillating electro-stimulation (DF) is provided during the last third of the static portion of the compression phase (STCP) of a compression/decompression cycle.

41. The method of claim 34, wherein pacing electro-stimulation (PC) is provided within the time period from the start of the compression phase (CP) until the start of the decompression phase (DCP) of a compression/decompression cycle.

42. The method of claim 34, wherein pacing electro-stimulation (PC) is provided within a time period of 0.10 to 0.15 seconds from the end of the dynamic compression phase (DNCP) of a compression/decompression cycle.

43. The method of claim 34, wherein the rate of mechanical stimulation is from 80 cycles per minute to 200 cycles per minute.

44. The method of claim 34, comprising an intermittent estimation of the compression resistance of the breast of the person.

45. The method of claim 44, wherein the result of said estimation is used for control of the compression force applied to the breast of the person.

46. The method of claim 34, wherein the period of time required for establishing a positive coronary perfusion pressure is from 30 seconds and more in the case of a preceding short period of asystolia lasting from 10 seconds to 50 seconds, and up to five minutes and more in the case of a preceding longer period of asystolia lasting at least two.

47. The method of claim 34, wherein mechanical stimulation is continued after the provision of electro-stimulation and re-establishment of circulation.

48. The method of claim 34, wherein electro-stimulation is by defibrillation.

49. The method of claim 34, wherein electro-stimulation is by pacing.

50. The method of claim 49 wherein the pacing rate is about 80 beats per minute at a compression/decompression rate of up to 80 cycles per minute, and is made to follow the compression rate if the latter surpasses the basic rate.

51. The method of claim 34, wherein the breathing gas, if provided by intubation, has a temperature of 5° C. or more below the ambient temperature.

52. The method of claim 51, wherein said breathing gas temperature is 10° C. or more below the ambient temperature.

53. The method of claim 34, wherein a cooling aqueous spray is administered to the person by means of the breathing gas which acts as a carrier.

54. The method of claim 34, wherein a medicament is administered to the person by means of at least one of the following: (1) the breathing gas and (2) an aqueous spray for which the breathing gas acts as a carrier, for at least one of the following: (1a) alleviating the effects of cardiac arrest and (2a) assisting in the re-establishment of circulation.

55. The method of claim 34, wherein administration of electro-stimulation is started once a minimum of 20 ml or more of blood has accumulated in the left ventricle of the person in case of an adult person.

56. The method of claim 34, wherein administration of electro-stimulation is started once the time average-mean volume of blood in the right atrium at asystole or ventricular fibrillation has been reduced by 50% or more by mechanical compression/decompression.

57. An apparatus for resuscitating a person under cardiac arrest comprising:
a reciprocating means for mechanical stimulation of the heart;
a means for the electric stimulation of the heart;
a means for controlling the provision of mechanical and electric stimulation over time to allow electric stimulation to be provided once at least one of the following conditions has been obtained (1) the time average-mean volume of blood in the right atrium of the person at asystole has been reduced by at least 50%, (2) ventricular fibrillation has been reduced by at least 50%, (3) 20 ml or more of blood has accumulated in the left ventricle of the person, and (4) a positive coronary perfusion pressure threshold;
a means for adducing breathing gas under pressure to the airways of the person;
a source of compressed breathing gas for providing breathing gas to the person being resuscitated coupled with the gas adducing means; and
a means for controlling the pressure of the breathing gas provided to the person, wherein the source of compressed breathing gas is designed to provide gas for driving the reciprocating means, and wherein the gas for driving the reciprocating means is the breathing gas provided to the person.

58. The apparatus of claim 57, wherein the means for controlling the provision of mechanical and electric stimulation comprises the means for controlling the pressure of the breathing gas provided to the person.

59. The apparatus of claim 57, further comprising an administration means for administering to the person under resuscitation a medicament for achieving at least one of (1) alleviating the effects of cardiac arrest and (2) assisting the re-establishment of circulation, the administration means being coupled to the gas adducing means and being capable of producing an aqueous spray containing the medicament.

60. The apparatus of claim 57, wherein the positive coronary perfusion pressure threshold is about 10 mm HG.

61. The apparatus of claim 57, wherein the positive coronary perfusion pressure threshold is about 15 mm HG.

62. The apparatus of claim 57, wherein the positive coronary perfusion pressure threshold is about 25 mm HG or more.

63. An apparatus for re-establishing circulation in a person under cardiac arrest comprising:
a source of compressed breathing gas;
means for providing said breathing gas under positive pressure to the airways of the person;
pneumatic reciprocating means for mechanically stimulating the heart of the person by repeatedly compressing and decompressing the chest at a rate from 60 cycles per minute to 200 cycles per minute;
electrical means for providing electrostimulation to the heart of the person, wherein the compressed breathing gas is used for driving said reciprocating pneumatic means and wherein the breathing gas vented from the reciprocating pneumatic means is used for providing breathing gas under positive pressure to the airways of the person.

64. The apparatus of claim 63, wherein the means for providing breathing gas to the person comprises one of (1) a facial breathing mask and (2) a device for intubation of the person's airways.

65. The apparatus of claim 63, wherein the pneumatic reciprocating means comprises a pad disposable so as to abut the breast of the person, and wherein said electrical means for providing electro-stimulation comprises two electrodes, a front electrode to be applied on the breast of the person, the front electrode being positionable adjacent to said pad of the reciprocating means, and a rear electrode disposed so as to be abutable to the back of the person.

66. The apparatus of claim 65, wherein the electrical means for providing electro-stimulation includes a means for analyzing ECG signals picked up by said electrodes and conducted to the ECG analyzing means.

67. The apparatus of claim 63, wherein the pacing frequency of said electrical means is controlled to follow the frequency of mechanical compression/decompression.

68. The apparatus of claim 63, wherein the breathing gas provided to the airways of the person has been used for driving the pneumatic reciprocating means.

69. An apparatus for resuscitating a person under cardiac arrest comprising:
a pneumatic drive unit that reciprocates a rod for compressing and decompressing the person's chest, wherein the pneumatic drive unit is driven by compressed breathing gas; and
a detachable means for administering a portion of the breathing gas consumed for driving the drive unit to the airways of the person at a positive pressure over a time period of 1 minute or more.

70. The apparatus of claim 69, wherein said breathing gas is at least 50% oxygen by volume.

71. The apparatus of claim 69, wherein said detachable means is one of (1) a facial mask, (2) an endotracheal tube, and (3) a tube for exotracheal intubation.

72. A system for administering steps in a course of cardiopulmonary resuscitation to a person, comprising:

a chest compression device for administering mechanical stimulation to the person's heart;

a module for administering electric stimulation to the heart;

a control unit for co-ordinating the administration of mechanical and electric stimulation to the heart over the course of the cardiopulmonary resuscitation;

an analysis unit for assessing the state of the person's heart during the course of the cardiopulmonary resuscitation, wherein the control unit comprises a program for automatically modifying steps in the course of the cardiopulmonary resuscitation in response to assessments made by the analysis unit; and means for supplying pressurized breathing gas to the person's lungs during the course of cardiopulmonary resuscitation, wherein the chest compression device is a pneumatic device operating on a gas, and wherein the means for supplying pressurized breathing gas recycles the gas used to operate the pneumatic device.

73. The system of claim 72, wherein the analysis unit is an electrocardiogram recorder/analyzer.

74. The system of claim 72, wherein the means for supplying pressurized breathing gas to the person's lungs comprises means for disposing medication in the breathing gas for administration to the person.

* * * * *